United States Patent [19]

Zare et al.

[11] Patent Number: 5,223,114
[45] Date of Patent: Jun. 29, 1993

[54] ON-COLUMN CONDUCTIVITY DETECTOR FOR MICROCOLUMN ELECTROKINETIC SEPARATIONS

[75] Inventors: Richard N. Zare, Stanford; Xiao-Hua Huang, Atherton; Joseph Pang, Palo Alto, all of Calif.

[73] Assignee: Board of Trustees of the Leland Stanford Junior University, Stanford, Calif.

[21] Appl. No.: 744,642

[22] Filed: Aug. 8, 1991

Related U.S. Application Data

[63] Continuation of Ser. No. 443,059, Nov. 28, 1989, abandoned, which is a continuation of Ser. No. 63,547, Jun. 17, 1987, abandoned.

[51] Int. Cl.$^5$ .................... G01N 27/26; G01N 27/447
[52] U.S. Cl. .............................. 204/299 R; 204/180.1
[58] Field of Search .......................... 73/23.4, 61.1 C; 324/444, 450; 204/299 R, 180.1

[56] References Cited

U.S. PATENT DOCUMENTS

| | | | |
|---|---|---|---|
| 2,176,471 | 10/1939 | Pyle et al. | 324/446 |
| 2,890,406 | 6/1959 | Axt et al. | 324/446 |
| 2,939,070 | 5/1960 | Rosenthal | 324/446 |
| 3,620,958 | 11/1971 | Dijksterhaus et al. | 204/183.3 X |
| 3,649,499 | 3/1972 | Virtanen et al. | 204/180.1 |
| 3,788,969 | 1/1974 | Di Stefano et al. | 204/299 R |
| 3,932,264 | 1/1976 | Haruki et al. | 204/299 R |
| 3,939,408 | 2/1976 | Brown | 324/444 |
| 3,941,678 | 3/1976 | Akiyama | 204/299 R |
| 3,993,945 | 11/1976 | Warmoth et al. | 324/449 |
| 3,998,719 | 12/1976 | Deml et al. | 204/183.3 |
| 4,484,582 | 11/1984 | Rottenberg et al. | 128/630 |
| 4,816,123 | 3/1989 | Ogan et al. | 204/183.3 |
| 4,909,919 | 3/1990 | Morris et al. | 204/299 R |

FOREIGN PATENT DOCUMENTS

| | | |
|---|---|---|
| 0216600 | 1/1987 | European Pat. Off. . |
| 1533087 | 6/1968 | France . |
| 128943 | 2/1985 | Poland . |
| 1120364 | 7/1968 | United Kingdom . |

OTHER PUBLICATIONS

Anthony T. Andrews "Electrophoresis: Theory, Techniques, and Biochemical and Clinical Applications, 2nd ed." (1986) p. 295.

C. van der Steen et al "A.C. Conductivity Measurements in Isotachophoresis" Analytica Chimica Acta vol. 59, No. 1 (Mar. 1972) pp. 298–301.

Kaniansky, D. et al "Simple Cell for Conductimetric Detection in Capillary Isotachophoresis" Journal of Chromatography, 267 (1983) 67–73.

Foret, F. et al "On-Line Fiber Optic UV Detection Cell and Conductivity Cell for Capillary Zone Electrophoresis" Electrophoresis, 1986, pp. 430–432.

St. Claire et al., "Characterization of an On–Column Electrochemical Detector for Open-Tubular Liquid Chromatography", J. Chrom. Science, 23, (May 1985), 186–191.

Huang et al., "On–Column Conductivity Detector for Capillary Zone Electrophoresis", Anal. Chem., 59, (1987), 2747–2749.

Knecht et al., "On–Column Electrochemical Detector with a Single Graphite Fiber Electrode for Open-Tubular Liquid Chromatography", Anal. Chem., 56, (1984), 479–482.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

An on-column conductivity detector for microcolumn electrokinetic separation systems is disclosed. The detector is based on the column itself, the column having a largest internal cross-sectional dimension of 500 microns or less and includes one or more sensing electrodes positioned directly upon or immediately adjacent to (i.e. contiguous with) the wall of the column into communication with the analyte stream so as to present no dead volume and no increase in cross-sectional area to the fluid flow. In one embodiment, this conductivity detector has a single on-column electrode, located immediately adjacent to the exit end of the column. In a preferred embodiment, this conductivity detector has one or more pairs of on-column sensing electrodes and these paired electrodes are located directly across from each other on the microcolumn, to minimize potential across the electrodes and concomitant electrochemical reactions.

18 Claims, 11 Drawing Sheets

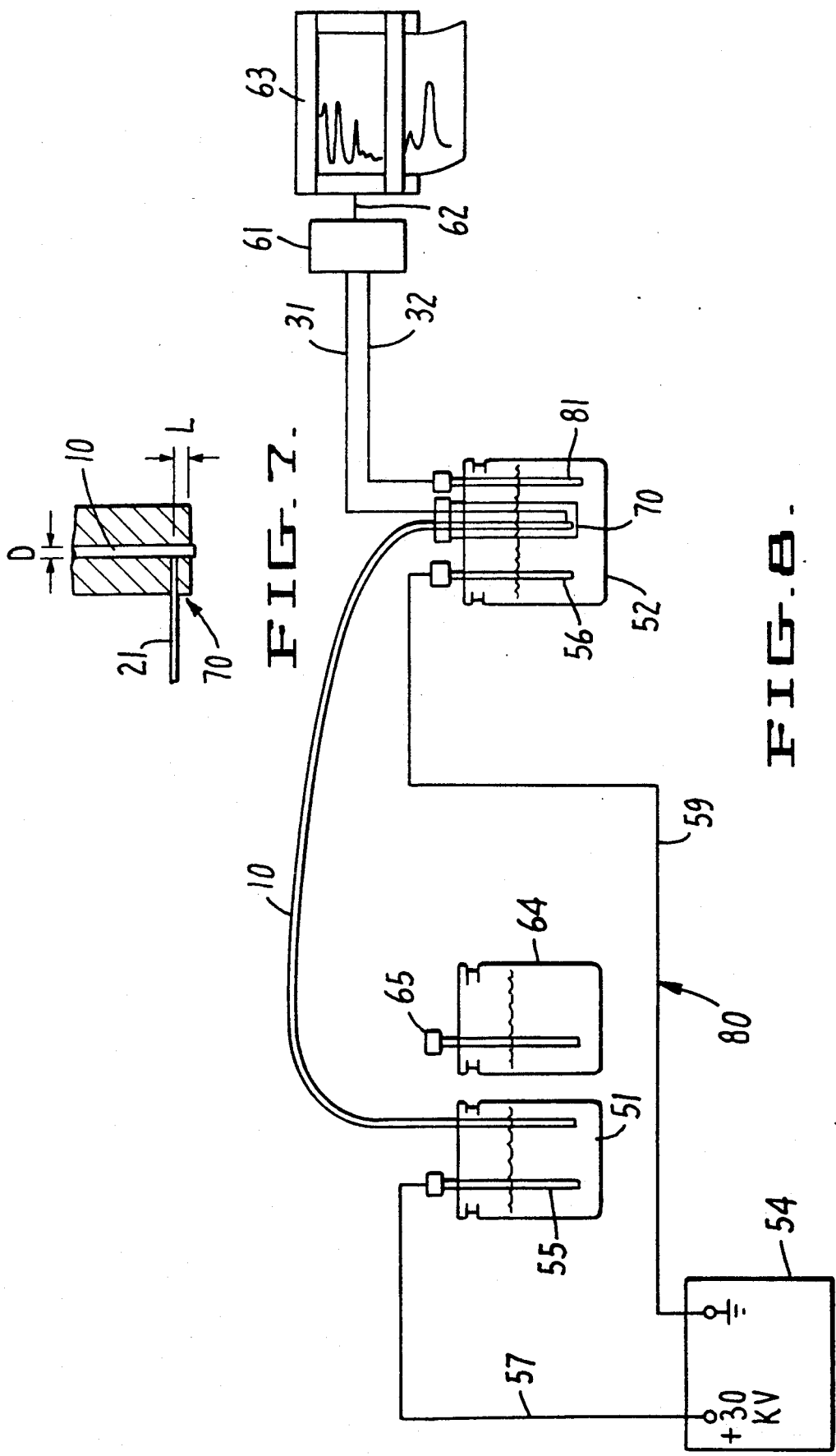

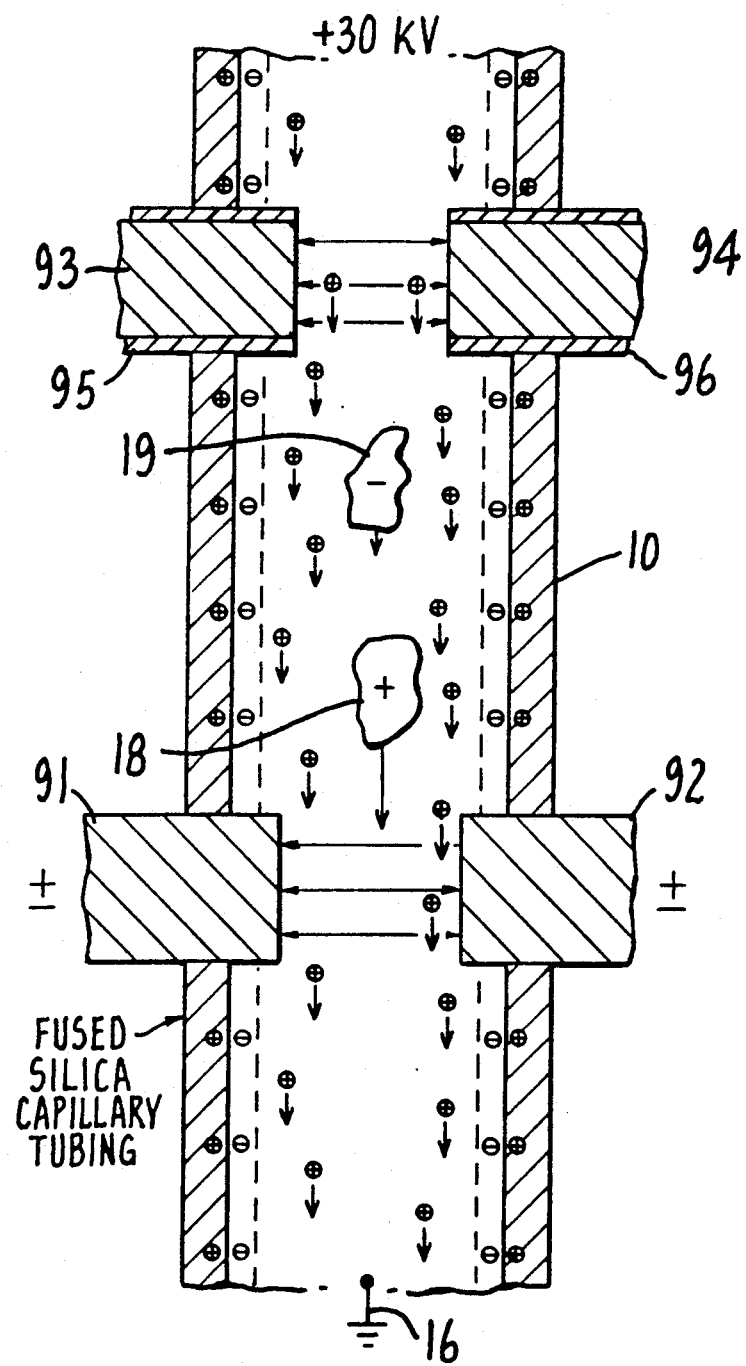
FIG_9.

TIME (MINUTES)

ON-COLUMN CONDUCTIVITY DETECTOR FOR MICROCOLUMN ELECTROKINETIC SEPARATIONS

This is a continuation of application Ser. No. 443,059, filed Nov. 28, 1989 now abandoned, which was a continuation of Ser. No. 063,547, filed Jun. 17, 1987, now abandoned.

BACKGROUND OF THE INVENTION

1. Field of the Invention

This invention is in the field of particle detectors. More particularly, it relates to a detector for detecting the electrokinetic passage of minute quantities of particles past a reference point in a microcolumn.

2. Description of Background Materials

Several analytical methodologies have been developed in which a fluid sample is driven through a narrow bore microcolumn so as to separate and/or isolate the various particles and species contained within the fluid sample on the basis of size, shape, charge, viscosity, mobility, polarity, solvent-solute inter-reaction, or the like. Two of these methodologies based on packed columns are isotachophoresis and high performance liquid chromatography. Another process of growing importance is electrokinetic separation (also commonly referred to as open tubular electrophoresis separation or capillary zone electrophoresis separation).

With electrokinetic separation, as with any separation process, it is necessary to have a means to detect the passage of particles or species through the column and/or the arrival of particles or species at a set location in the column after the separation has taken place. A wide range of detectors are known based on any one of many changes in properties which may occur as the particles or species pass the detection zone. These can include, for example, a change in optical properties (e.g. U.V., visible or I.R. based detectors as well as refractive index detectors), a change in electrical properties (e.g. conductance or resistance-based detectors), or a change arising from an electrochemical reaction (e.g. amperometric, coulometric, or potentiometric detectors).

The present invention relates to an improved electrical detector for use with microcolumn electrokinetic separation systems. Electrical detectors can be distinguished from electrochemical detectors. Electrochemical detectors involve electric effects due to chemical changes which occur when a particle or species enters the detection zone. Electrical detectors respond to changes in the conductance of current or changes of resistance which result when particles or species enter the detection zone. With electrical detectors no chemical reaction is necessarily associated or required.

With any microcolumn electrokinetic separation process and any of these detector methodologies, there is an interest in increasing the sensitivity. This can lead to smaller sample sizes being used or to detection of smaller trace components in the samples.

A number of workers have proposed a variety of small volume high sensitivity detectors for use on various types of columns. For example, Jorgenson, et al. (Knecht, L. A., Guthrie, E. J., and Jorgenson, J. W. *Anal. Chem.*, 1984, 56, 479–82; St. Claire, R. L., III, and Jorgenson, J. W. *J. Chromatogr. Sci.*, 1985, 23, 186–91) built an on-column electrochemical detector for a 15 micron internal diameter open tubular column. In this system the working electrode was a 5 micron or 9 micron carbon fiber that was inserted with a micropositioner into the end of the capillary. Adler, et al. (Adler, J. F., Fielden, P. R., and Clark, A. J. *Anal. Chem.*, 1984, 56, 985–988) described a combination conductivity/permittivity detector. This detector provided simultaneous measurements of these two properties within a single cell. The detector was applied to ion chromatography systems. A detection limit of 40 ppb of chloride was reported. This system employed a pair of conical electrodes as its detection cell. Doury-Berthod, et al. (Doury-Berthod, M., Giampoli, P., Pitsch, H., Sella, C., and Poitrenaud, C. *Anal. Chem.*, 1985, 57, 2257–2263) presented a theoretical description of dual column chromatography with conductivity detection. Their analytical response appears to be the sum of the conductometric contribution of the solute and the eluant. Kaniansky, et al. (Kaniansky, D., Koval, M., and Stankoviansky, S. *J. Chromatogr.*, 1983, 267, 67–73) use 0.01 mm Pt-Ir alloy wires as electrodes in isotachophoresis. The capillaries were as small as 0.1 mm and made of fluoropolymers (PTFE, FEP). The wires were heated and pushed through the walls of the capillary. T. Tsuda has also described the use of a commercial conductivity detector external to the capillary for analyzing small positively charged metal ions (Suzuken Memorial Foundation 3, 33 (1984)).

Several papers by Mikkers, et al. (Mikkers, F. E. P., Everaerts, F. M., and Peek, J. A. F., *J. Chromatogr.*, 1979, 168, 317–332; Mikkers, F. E. P., Everaerts, F. M., and Verheggen, Th. P. E. M. *J. Chromatogr.* 1979, 169, 1–10; Mikkers, F. E. P., Everaerts, F. M., and Verheggen, Th. P. E. M. *J. Chromatogr.* 1979, 169, 11–20) all referenced conductivity detectors for isotachophoresis in capillary electrophoresis based on the work of Everaerts and colleagues (Everaerts, F. M., and Verheggen, Th. P. E. M. *J. Chromatogr.* 1972, 73, 193–210; Everaerts, F. M., and Verheggen, Th. P. E. M. *J. Chromatogr.*, 1974, 91, 837–851; Everaerts, F. M., and Rommers, P. J. *J. Chromatogr.*, 1974, 91, 809–818; Everaerts, F. M., Geurts, M., Mikkers, F. E. P., and Verheggen, Th. P. E. M. *J. Chromatogr.*, 1976, 119, 129–155; Kaniansky, D., and Everaerts, F. M. *J. Chromatogr.*, 1978, 148, 441–446; Everaerts, F. M., Beckers, J. L., and Verheggen, Th. P. E. M. "Isotachophoresis: Theory, Instrumentation and Applications", 1976; Elsevier, New York, p. 136). The Everaerts' device consists of glass or PTFE capillary tubing with an inside diameter of 0.4 to 0.6 mm and an outside diameter of 0.7–1 mm. Two blocks of capillary tubing have one of each of their ends fixed in a block so that the two blocks can be clamped together. Before clamping, two disks of insulating material 0.005 mm thick have platinum sputtered on both sides and separated from one another by a disk of plain insulating material are drilled to form a hole in their centers which matches the i.d. of the capillary. These disks are placed between the two blocks which are then clamped so that no leakage occurs.

Bocek et al. (Foret, F., Deml., M., Kahle, V., and Bocek, p., *Electrophoresis* 1986, 7, 430–432) developed a conductivity cell for capillary zone electrophoresis. They used capillaries of about 0.3 mm i.d. Platinum electrodes were molded into a polyester block containing a channel with a circular cross-section equal to the inside diameter of the capillary. Larger openings in the ends of the block made a tight fit with pieces of capillary inserted. In both the Everaerts and Bocek cells, it is important to note that the electrodes are outside the capillary and that the inside surface of the glass or PTFE tubing is not continuous. These discontinuities in the tubing surface can be of particular concern in column electrophoresis or isotachophoresis systems. In these systems substantial voltages are connected across the column. Any increase in column cross-sectional area or any discontinuity in the column surface can lead to disturbances in the flow. This can reduce the accuracy and reproducibility of results. This problem becomes especially acute as one attempts to use smaller and smaller cross-section columns and higher and higher driving voltages. Another problem arises when the cross-section increases at the detector because of dead or void volume which can diminish the sensitivity of the detector. For these reasons, we have found that it is most advantageous in these settings to present as continuous an internal surface as possible with no discontinuities or cross-section increase.

STATEMENT OF THE INVENTION

An improved conductivity detector for microcolumn electrokinetic separation systems has now been found. This conductivity detector is characterized by being "on-column", that is, it is based on the column itself, said column having a largest internal cross-sectional dimension of 500 microns or less, preferably 200 microns or less and more preferably 100 microns or less, by comprising one or more sensing electrodes having a largest cross-sectional dimension which is from about 0.01 to about 0.75 times the maximum internal dimension of the column with these electrodes being placed directly on the column either by being inserted through the wall of the column or by being affixed at and in contact with the exit end of the column into communication with the analyte stream while presenting a continuous wall surface and no increase in cross-sectional area to the fluid flow.

In one embodiment, this conductivity detector has a single on-column electrode, located at or immediately adjacent to the exit end of the column. In this embodiment the second electrode is provided by an electrical connection to the fluid outflow volume.

In a preferred embodiment, this conductivity detector has one or more pairs of on-column electrodes and these paired electrodes are located directly across from each other on the microcolumn, to minimize potential across the electrodes and concomitant electrochemical reactions.

In other aspects this invention provides improved separation systems employing these detectors in combination with electrokinetic separation systems.

In yet an additional aspect this invention provides an improved method for fabricating several embodiments of such conductivity detectors by laser drilling the microcolumn to provide positioning for the sensing electrodes and to achieve the desired placement accuracy and alignment for the electrodes.

The conductivity detectors of this invention are extremely sensitive, being able to detect conductivity changing species in the analyte solution at concentrations of less than $10^{-7}$ moles per liter. They have very tiny detection volumes and this coupled with their minimal dead volumes and high sensitivities allow very small numbers of ions or other species to be detected.

DETAILED DESCRIPTION OF THE INVENTION

Brief Description of the Drawings

In this detailed description of the invention, reference will be made to the attached drawings, in which common parts have common reference numbers.

FIG. 7 corresponds to FIG. 4 and is another enlarged cross-section of the electrode area of an alternative embodiment of the detector of this invention having but a single on-column electrode.

FIG. 8 corresponds to FIG. 5 and illustrates the use of the single electrode detector of FIG. 7.

FIG. 9 is a cross-sectional view of an alternative embodiment of the detector of this invention.

DESCRIPTION OF PREFERRED EMBODIMENTS

Figure 1:
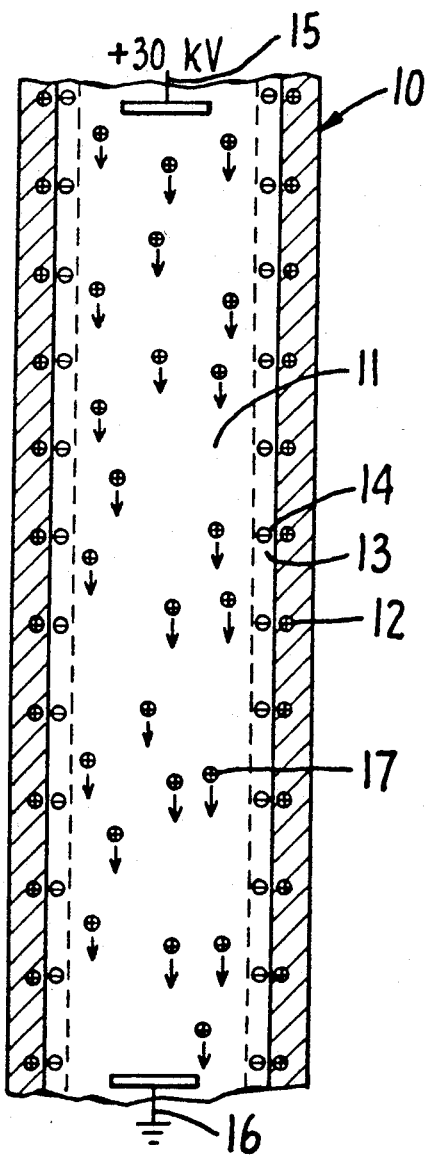
FIG. 1 is a cross-sectional view of a liquid-filled tube illustrating the process of electroosmotic pumping.

The present invention provides on-column conductivity detectors for use in microcolumn electrokinetic separation systems. The use of electroosmosis for pumping fluids was first described in 1974 by Pretorius, et al (J. Chromatogr., 99, 23). In this process there is flow of a liquid in contact with a solid surface under the influence of a tangentially applied electric field. The liquid flow is an electroosmotic flow that is attributed to the information of an electric double layer at the solid/liquid interface, causing the overall liquid to be charged. This transport process can be visualized with reference to FIG. 1. In FIG. 1, a small bore double open-ended microcolumn or tube 10 is shown in cut away cross-section. The tube is filled with a conductive liquid 11 sometimes referred to herein as a "support electrolyte". The wall of tube 10 contains positive ions 12. (Depending upon the material of tube 10, the charge could be negative, instead.) Positive ions 12 attract anions 13 from conductive liquid 11 and set up an electric double layer 13. This preferential attraction of anions to the wall results in a net excess positive charge in the body of liquid 11. Thus, when an electric potential such as the 30 kV potential noted in FIG. 1 is applied between electrodes 15 and 16, located at the ends of the column of liquid 11 contained within tube 10, the positively charged liquid moves toward the cathode.

Figure 2:
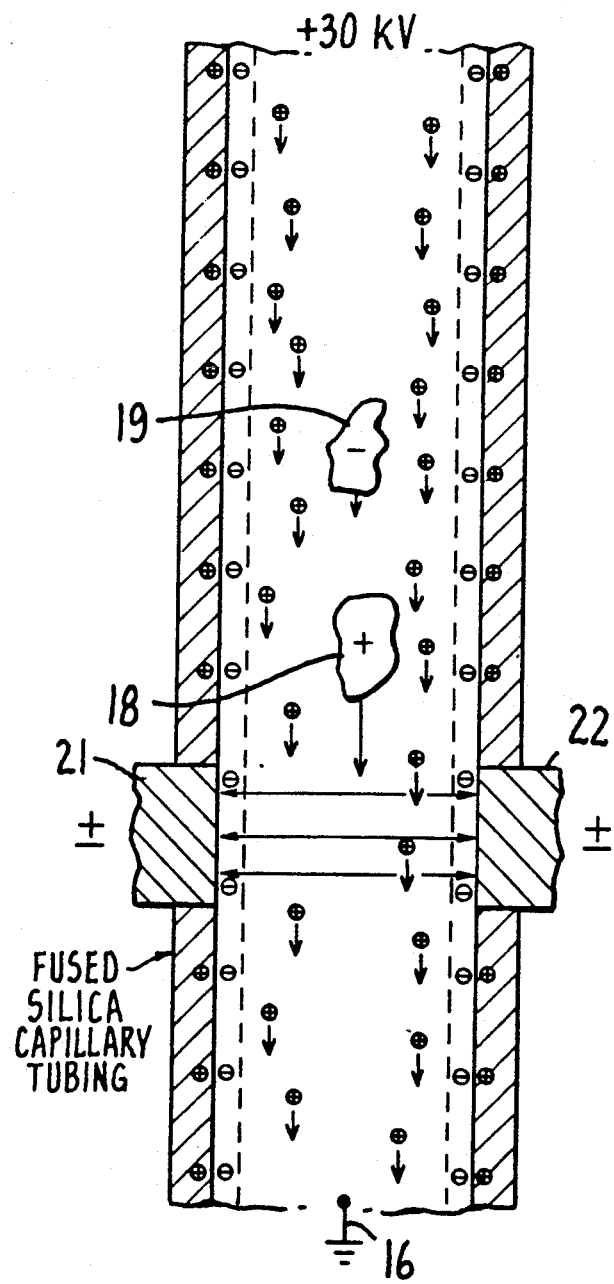
FIG. 2 is a cross-sectional view of a liquid-filled tube illustrating the process of electrokinetic separation and the application of a detector of this invention to such a process.

The electrokinetic separation process relies upon the electroosmosis effect just described and upon the differential effect of the electric field on the motion of solutes or suspended particles in the liquid medium depending upon their positive, neutral or negative charge. These related effects may be visualized with reference to FIG. 2. FIG. 2 is a copy of FIG. 1 but with various charged species 18 and 19 in liquid 11. Cationic species 18 is electrophoretically drawn toward cathode 16. Anionic species 19 is electrophoretically repelled by cathode 16. As is shown in FIG. 2, and as is usually the case, the velocity of the liquid 11 is larger than the electrophoretic velocities of the species in solution such that all the species can be seen to move in the direction of the electroosmotic flow but at differing rates. As these species 18 and 19, or uncharged species as well, pass through, i.e. between, the detector made up of electrodes 21 and 22, they alter the conductivity properties measured across these two electrodes which depends upon the difference between the background and the sample.

Electrodes 21 and 22 have several characteristics which give rise to the high sensitivity of the present detectors. One characteristic is that the two electrodes are "on-column". That means that they are an integral part of the column rather than a separate detector unit. The second characteristic is that the two electrodes terminate at least flush with the walls of tube 10 so that a continuous internal surface is presented to the liquid 11 moving through the column. By "at least flush" is meant that the electrodes either are flush or extend into the liquid flow. They are not withdrawn from the flow. In FIG. 2 the electrodes are flush with their ends, are cut flat, and are perpendicular to their axis. A third characteristic is that the two electrodes are placed on the same plane perpendicular to the axis o the microcolumn. This minimizes the potential between the electrodes due to the electrokinetic voltage applied to the column and thus minimizes electrochemical reactions at the electrodes. A fourth characteristic is that the microcolumn has an internal diameter or maximum cross-sectional dimension of less than 500 microns, preferably less than 200 microns and more preferably from about 25 microns to about 80 microns and that the electrodes have a diameter equal to from about 0.01 to about 0.75, and especially from about 0.01 to about 0.60 times this internal diameter of maximum cross-sectional dimension. These dimensions do not degrade the high resolution intrinsic to microcolumn electrokinetic separations. A fifth is that electrodes 21 and 22 are fabricated from a conductive material such as carbon or a metal inert under the conditions found in the electrolyte, e.g., platinum, platinum/irridium, gold, silver, stainless steel, and the like.

In an alternative embodiment of the detectors of this invention which will be described with reference to FIGS. 7 and 8, the detector can include one "on-column" electrode with the second electrode being provided by the fluid outflow container. In this embodiment, the single on-column electrode has all the characteristics just enumerated except, of course, for the requirement that it be diametrically opposed to the other electrode.

The placement of the electrodes in the detector through the wall of the column is a relatively precise matter. This can be accomplished by precisely drilling the access holes in column 10 such as with a laser drill, ion beam drill, electroerosion, chemical etching, or the like to a size adequate to accept the electrodes as well as minimal but adequate amounts of adhesive/sealant. Other hole-forming methods may be used such as HF etching (in the case of glass or other inorganic silicious columns) or other chemical etches for organic columns. In preferred embodiments, the access holes are drilled to a size from about 5 to about 25 microns larger in diameter than the diameter of the electrode being inserted and the electrodes are sealed into these holes. Epoxy resins, cyanoacrylate adhesives and like materials which are inert to the predominantly aqueous support liquids commonly employed and which give strong adherent bonds to the electrodes and to the column wall material are generally employed to seal the electrodes into their "on-column" position.

The sensing electrode of this invention is positioned on a microcolumn 10 at its far end, that is its end last traveled by the species being separated. This microcolumn 10 should be of a length that is effective to achieve the desired separation of species under the electrokinetic separation conditions employed. It will be appreciated that the longer the column the greater the time a sample will take to move through the column and the greater the distance that the various species will be separated from one another. In the case of electrokinetic separations, at the same time band broadening takes place so that resolution may not be improved by adding length. These factors suggest practical limits to the microcolumn length. For example, good results are achieved with column lengths as short as about 5 cm. Similarly, the transport time through a column often becomes inconveniently long for many routine analytical settings with column lengths longer than several meters. Generally, column lengths of from about 10 cm to about 200 cm, and especially from about 40 cm to 150 cm are preferred. Of course, longer and shorter columns, for example up to 4 or 5 meters or down to about 5 cm, can be employed in combination with the detectors of this invention. Because of their ease of construction, circular cross-section column, i.e. "capillary tube type" columns, are preferred.

The microcolumn is constructed of a material that has the properties of being durable and retaining its physical integrity at the conditions of the electrokinetic separations. These properties include compatibility with the support electrolyte; substantial nonconductivity so as to conduct negligible electricity and to generate negligible heat as the electrokinetic potential is applied to it; and, being able to take on a positive or negative charge on its inner surface.

Inorganic materials such as quartz, glass, and fused silica and organic materials such as teflon (polytetrafluoroethylene and fluorinated ethylene/propylene polymers), polychloro-trifluoroethylene, aramide, nylon (polyamide), polyvinylchloride, polyvinylfluoride, polystyrene, polyethylene, polycarbonate, and the like may be employed.

As pointed out herein, electroosmotic flow is achieved when the inner surface of the microcolumn carries or adsorbs charged species. The inner surface of the microcolumn can be modified to vary its charge such as by contacting the surface with an acidic liquid so as to impart more positive charges, or by contacting the surface with a basic material so as to impart more negative charges or by contacting the surface with a silylating agent so as to reduce the number of charges. (See *Analytical Chemistry*, 53, No. 8, July 1981, 1298 for a description of the use of a trimethylsilane to reduce the charge density on the walls of a narrow channel electrophoresis zone and thus to vary the transport through the zone.) Other surface modification techniques that are know to the art may be used as well.

Figures 3, 4:
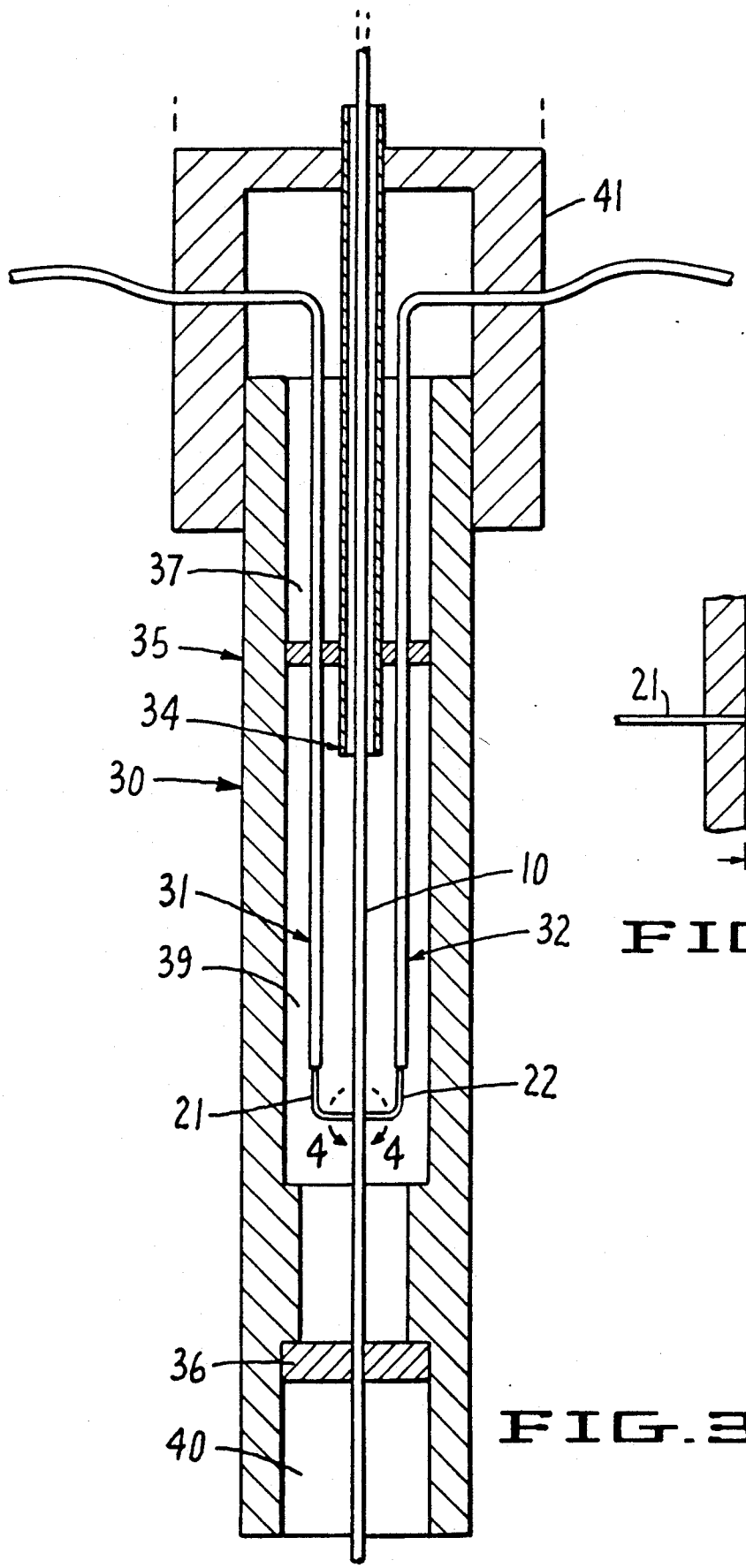
FIG. 3 is a cross-sectional view of a two-electrode conductivity-measuring detector of the present invention.
FIG. 4 is an enlarged cross-section of the electrode area of the detector shown in FIG. 3.

Turning now to FIGS. 3 and 4 in addition to FIG. 2, FIGS. 3 and 4 illustrate that the detector of FIG. 2 can be incorporated into a structural terminus 30 for microcolumn 10. In FIG. 3, electrodes 21 and 22 are shown joined to connecting leads 31 and 32 for connection to the conductivity meter (not shown). Terminus 30 as shown in FIG. 3 includes a number of additional components which lend strutural strength to the terminus and illustrate an excellent mode for constructing a practical device for practicing the invention.

These components include a flexible support tube 34 which extends from the microcolumn terminus 30 to prevent breakage of the column. This tube typically is a plastic material such as teflon or the like. Supports 35 and 36 which center the tube during fabrication again usually are of plastic. Terminus body parts 37, 39 and 40 are generally cast around the other terminus components to surround them and hold them rigid. Cap 41 is designed to position the terminus 30 in an electrophoretic or electrokinetic apparatus.

Figure 5:
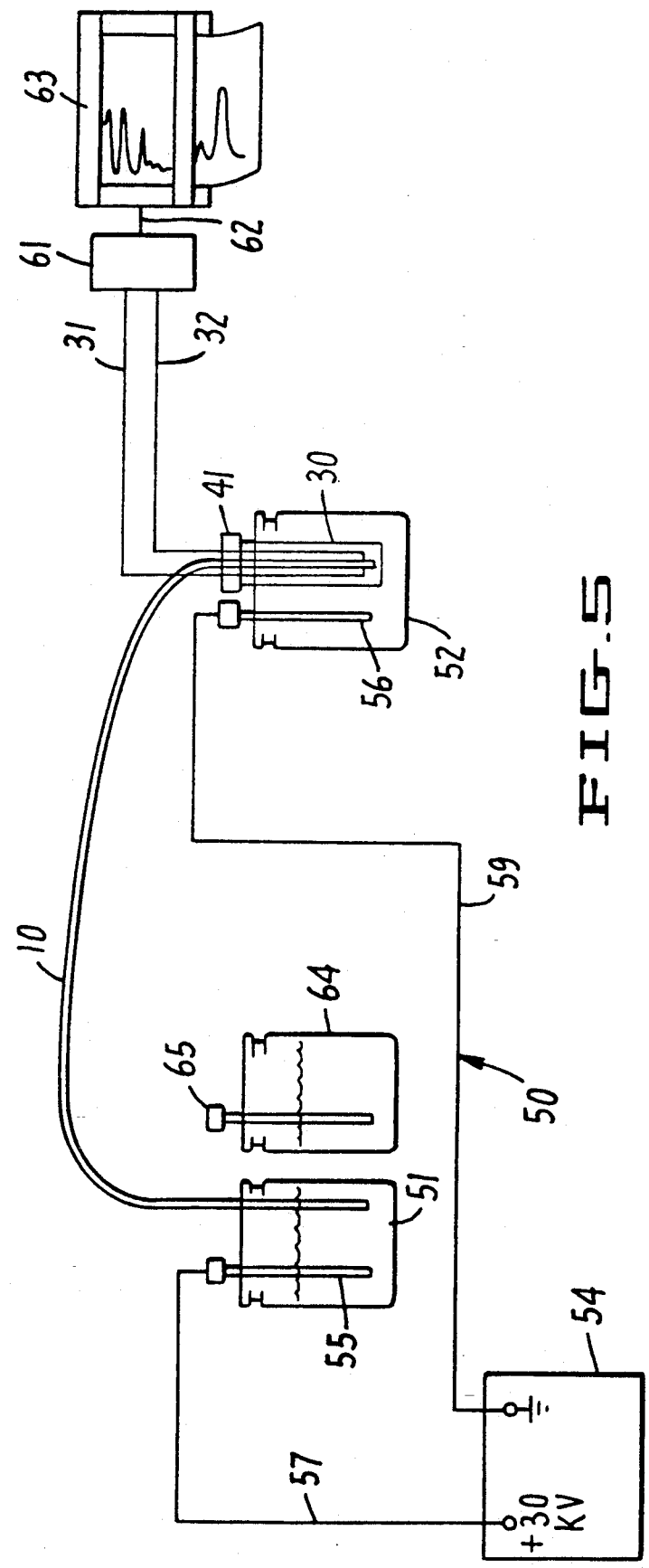
FIG. 5 is a schematic block diagram of one type of apparatus for employing the two-electrode detector shown in FIGS. 3 and 4.

Such an apparatus is shown schematically in FIG. 5. The apparatus includes a fused-silica capillary 10 which typically might have a 75 cm total length and a 50 micron inside diameter. The capillary is liquid-filled with a support electrolyte and terminated in terminus 30 containing a detector of this invention as shown in FIG. 3. Feed container 51 and outflow container 52 contain support electrolyte as well, so that liquid-filled capillary 10 creates a continuous liquid and electrical connection between them. An effective electrokinetic voltage is applied from power supply 54 through conductors 57 and 59 and electrodes 55 and 56 contacting the electrolyte in containers 51 and 52 to yield a complete electrical circuit.

The voltage applied across the sample in column 10 by power supply 54 should be a voltage effective to cause discernable electrokinetic motion without excessive heating. Voltages below about 1000 volts are generally too low and voltages above about 100 kV are not commonly found in conventional high voltage power supplies. Based on these practical limits, voltages from about 3 kV to about 90 kV, and especially about 5 kV to about 60 kV, are preferred. The polarity of the electric potential determines the direction that the electrically charged species and charged support electrolyte move. It is generally preferred for safety reasons to have as much of the analysis system at ground potential as possible. In FIG. 5, a 30 kV voltage is shown for illustration purposes. The inner surface of column 10 is such as to attract ions, for example negative ions (anions) and thus to cause formation of a diffuse double layer and in turn impart a net positive charge to the body of the support electrolyte in column 10. When the 30 kV potential is applied to the liquid in outflow container 51 by electrode 55, it can cause this positively charged liquid to be electroosmotically drawn from column 10 into container 52 and to draw additional electrolyte out of container 55 into column 10.

A typical current flow is 10–100 microA. In typical electrokinetic systems, the linear velocity of liquid through capillary 10 is about 0.2 to about 5 mm/second.

Capillary 10 passes through detector 30 which includes the two electrodes as shown in FIGS. 1 through 4. The output of detector 30 which varies as a function of the material driven between the two electrodes, is passed through leads 31 and 32 to conductivity meter 61, the output of which is fed through line 62 to a strip chart recorder 63. It will be appreciated that this output could be stored or otherwise processed such as in a computer.

In use, a sample is injected into capillary 10. This can be accomplished by mechanically or gravitationally injecting sample onto the column or by dipping the entrance end of capillary 10 into the liquid sample contained in container 64, connecting lead 57 to electrode 65 and turning on the high voltage for a short period, for example 5 to 10 seconds, at an electrokinetically effective voltage such as about 6 kV. This causes a defined 1 to 5 mm long "plug" of sample to be drawn into column 10. This sample is then subjected to the separative forces of electrokinesis by placing the entrance end in the support electrolyte in container 51, and creating the complete circuit through electrode 55 to separate the various species for detection in the detector of this invention.

Figure 6:
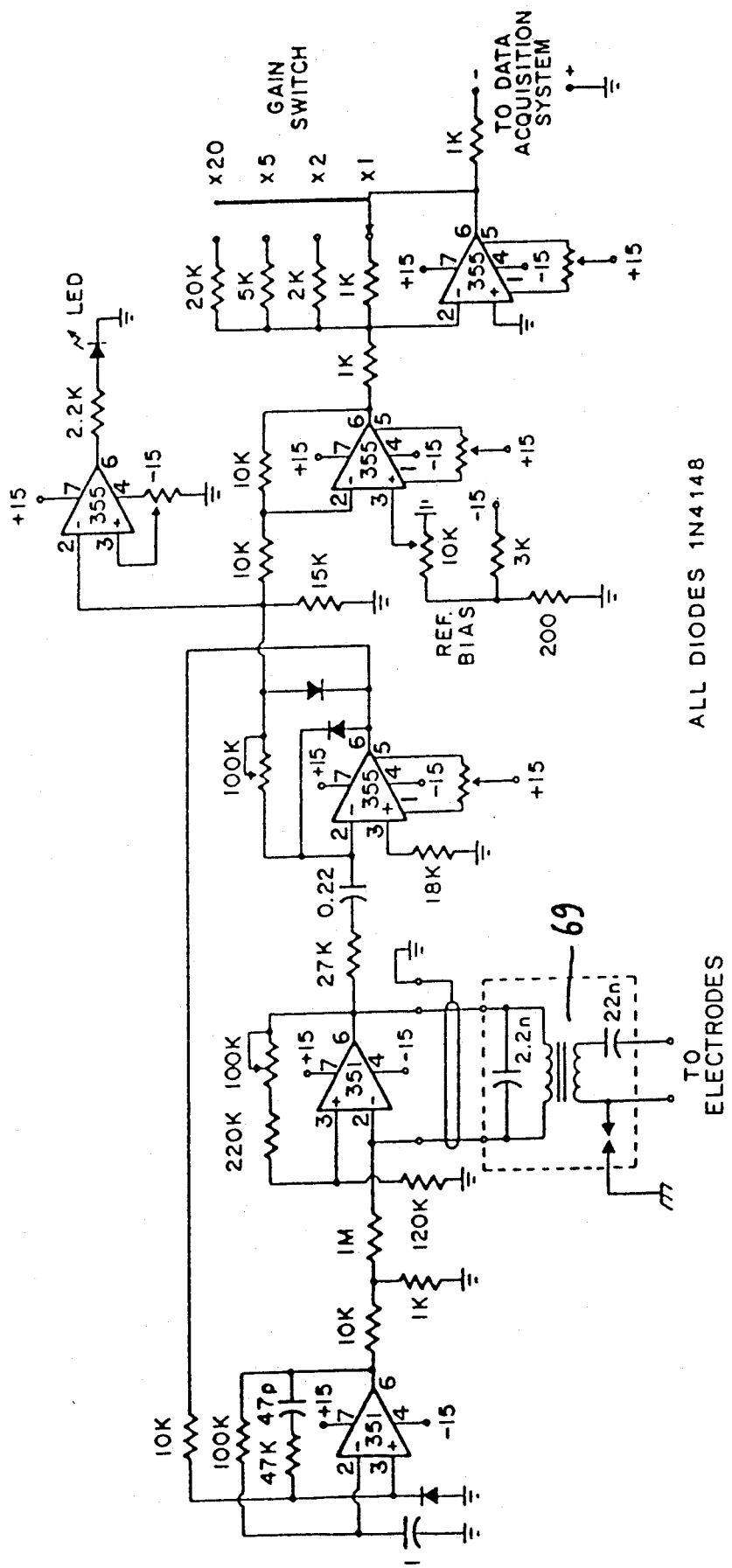
FIG. 6 is an electrical schematic illustrating one form of meter circuit useful in measuring signals sent by the detectors of this invention.

The conductance values measured by the detectors of this invention must be converted into a readable form and displayed or otherwise used. FIG. 6 is a schematic of one type of AC conductivity meter which can generate a readable conductivity signal when used with the electrodes. This meter circuit is a modification of the meter set out by Everaerts et al. in "Isotachophoresis. . . , supra, at 148. This circuit employs high impedance input ICs, LF351 and LF355. A transformer 69 is used as a galvanic insulator between the sensing electrodes, which are not shown and which have a high DC potential to ground, and the electronic circuit. The oscillation frequency is set to 3.5 kHz although other frequencies can be used as well. A low-pass filter is placed after the circuit to minimize electronic noise. The output of the conductivity meter is amplified (gain: 10 or 20) before being transmitted to a microcomputer for display either on a screen or on a hard printout device.

In an alternative embodiment, the detector of this invention has a single "on-column" electrode and relies upon electrical contact with the liquid in the outflow container to provide the second electrode. This embodiment is shown in FIGS. 7 and 8. Detector 70 of FIG. 7 includes the microcolumn 10 as previously described with a single on-column electrode 21. This electrode is located very near the end of the column 10. Preferably, the distance L is similar to the largest dimension of the cross-section of the column, e.g. the diameter in the case of circular cross-section columns. It is preferred when L is 500 microns or less and more preferred when L is 300 microns or less. This minimizes the DC potential which will result on electrode 21 since this potential is a direct function of the distance L.

When detector 70 is included in an overall electrokinetic separation system, such as system 80 shown in FIG. 8, the same setup described with reference to FIG. 5 (and identified in FIG. 8 accordingly) can be used with the exception that an additional electrode 81 is present. This electrode contacts the liquid in container 52. This liquid in turn contacts the open end of column 10 and thus creates a completed electrical circuit for the conductivity measurement. Alternatively, the second electrode could be achieved by connection to electrode 56. In this setup the detection event is when the particle or species enters the region of the column between the electrode 21 and the end of the column, that is when it is in the "L" region. Once the particle or species enters the gross volume of container 52 its presence is not detectable.

More than one pair of the sensing electrodes of this invention can be present on a given electrokinetic separation column. For example, two or more pairs of electrodes can be used. This can permit multiple readings to be taken as particles pass various points on the column. This can permit adjustments to be made on the detector circuits and the like to optimize detector performance. Multiple single electrodes could be used, if desired.

Turning to FIG. 9, a column is shown having two pairs of on-columns electrodes, 91 and 92 and 93 and 94. As previously noted, these electrodes are at least flush with the surface of tube 10. Electrodes 91 and 92 extend into the liquid flow and do not give rise to any dead volume in the column. Electrodes 93 and 94 are similar but carry an insulating coating 95 and 96 on their cylindrical surfaces so that only their ends contact the fluid and detect conductivity changes. This arrangement can give rise to very sensitive detection.

Figure 10:
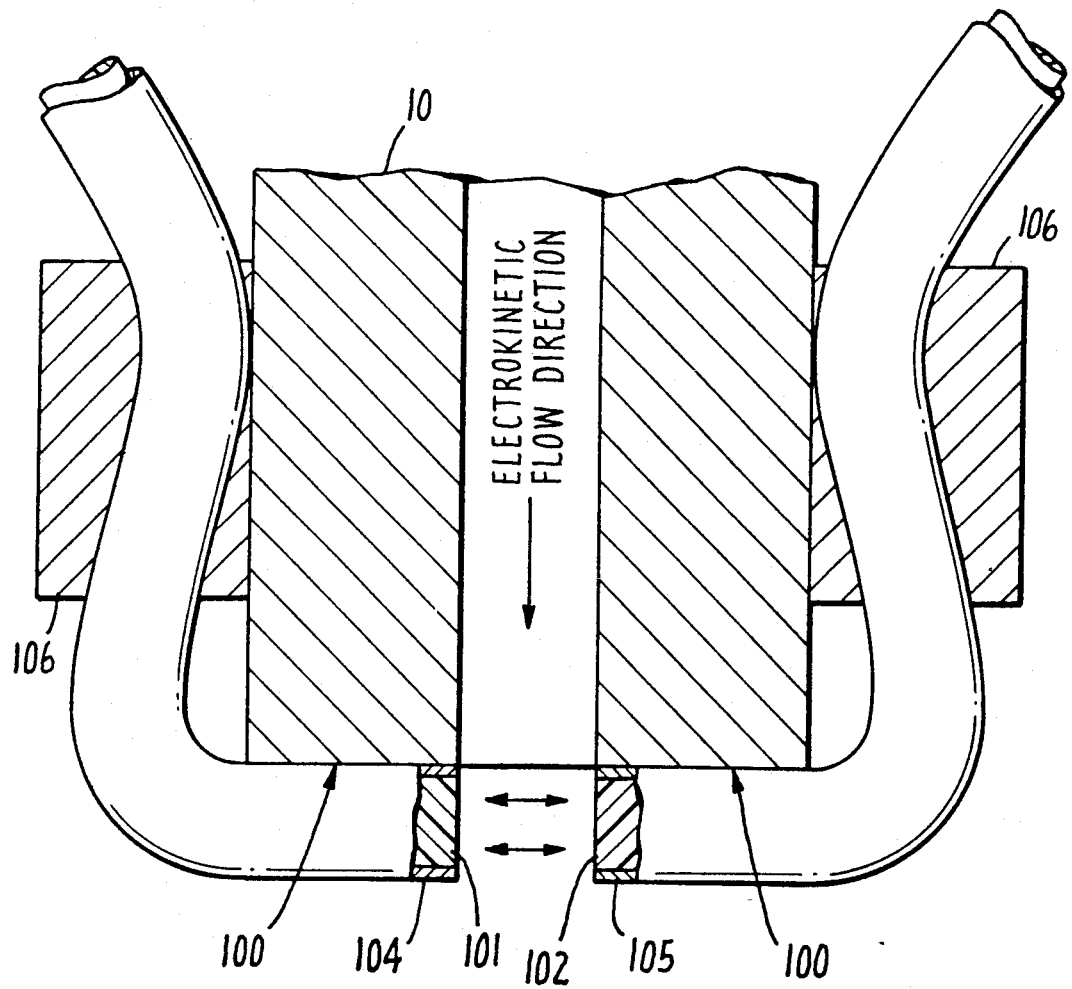
FIG. 10 is a cross-sectional view of another alternative embodiment of the detector of this invention.

Turning to FIG. 10, a column having a pair of on-column sensing electrodes 101 and 102 in there shown. Electrodes 101 and 102 are located contiguous with the exit end 100 of microcolumn 10 and are held in position there by molded adhesive band 106. Electrodes 101 and 102 are covered on their side surfaces with electrical insulators 104 and 105 so that conductivity is measured between their ends alone. This location of the on-column electrode contiguous with the end of the column has advantages of simple construction and durability.

Applications of the Detectors

The detectors of this invention and the analysis systems which employ them can be used to detect charged and uncharged species and particles in solution. The liquid phase of the solutions is conductive and is an electroosmotically pumpable support liquid. A liquid is electroosmotically pumpable when it is an electrolyte, that is, when it contains or carries enough electrically charged species to conduct an electric current. Typical electroosmotically pumpable support liquids contain, for example, at least about 0.0005 moles per liter of ionic species and preferably from about 0.001 to about 10 moles per liter of ionic species. Such levels provide reasonable rates of electrokinetic transfer. Most commonly the support liquid system. A mixed system can be useful to help solubilize or suspend organic target materials which have limited solubility in water alone. A neat organic liquid that is capable of conducting electricity can also be used. Representative materials for use in the support electrolyte include water and mixed solvents made up of water admixed with one or more water-miscible organic materials such as lower (e.g. 1 to 4 carbon atom) alkanoic acids such as acetic acid, propionic acid, chloroacetic acid and the like; lower primary and secondary alkyl amines such as methyl amine, lower alcohols such as ethanol, methanol, and propanol; lower polyols such as the lower alkane diols; nitrogen containing liquids including acetonitrile, pyridine, piperidine and quinoline, lower ketones such as acetone and methyl ethyl ketone; lower alkyl amides such as DMF, N-methyl and N-ethyl formamide, N-ethyl acetamide and the like. With any of these liquids, the support liquid may contain added ionic materials such as salts, chelates and other complexes, acids, bases, buffers and the like. Surfactants, or other materials which promote micellularization can also be included. It is often preferred to use added ionic species which are zwitterions at the pH at which the liquid is passing through the electrokinetic channel. Representative materials include alkali metal and alkaline earth metal and transition metal salts of inorganic acids; similar salts of organic acids, ammonium and organic base salts of such acids; halogen acids, organic acids, and other acids; metal acids and hydroxides, amines and other bases, and the like. Typical zwitterions include amino acids and the Good's buffers marketed by Sigma Chemical Company, St. Louis, Mo. These added ionic or ionizable materials may be selected from these broad classes generally at will so long as they are compatible with the other components of the sample and the support electrolyte as their primary function is to increase the conductivity of the support electrolyte.

The species or particles which are detectable with the detectors of this invention can be selected virtually without limitation from the materials which can be suspended or dissolved in the support liquid. These materials can include simple ions such as sodium, potassium, lithium, selenium, beryllium, copper, silver, iron, and magnesium ions; chloride, bromide, ammonium sulfate, nitrate, phosphate and the like up through much more complicated materials such as are often of biological or ecological or chemical interest.

The target species thus can be macromolecules such as polyamino acids, i.e., polypeptides and proteins, polysaccharides; nucleic acids and oligonucleotides such as RNA, DNA and DNA fragments, and combinations thereof. Such combinations of assemblages include bacteria, viruses, chromosomes, genes, mitochondria, nuclei, cell membranes, and the like.

The wide variety of proteins and polypeptides grouped according to similar structural features, proteins having particular biological functions, proteins related to specific microorganisms, particularly disease-causing microorganisms, etc.

The following are classes of proteins related by structure: protamines, histones, albumins, globulins, scleroproteins, phosphoproteins, mucoproteins, chromoproteins, lipoproteins, nucleoproteins, glycoproteins, proteoglycans, unclassified proteins, e.g., somatotropin, prolactin, insulin, and pepsin.

There are, of course, numerous potential target proteins found in the human plasma which are important clinically and include: prealbumin, albumin, $a_1$-lipoprotein, thyroxin-binding globulin, Gc-globulin (Gc 1-1, Gc 2-1, Gc 2-2), chlinesterase, myoblobin, transferrin, fibrinogen, immunoglobulin G (IgG), immunoglobulin A (IgA), immunoglobulin M (IgM), immunoglobulin E (IgE) or qE-globulin (qE), complement factors, blood clotting factors, peptide and protein hormones including, for example, parathyroid hormone (parathormone), insulin, glucagon, somatotropin (growth hormone), follicle-stimulating hormone, luteinizing hormone (interstitial cell-stimulating hormone), gonadotropin, secretin, and gastrin.

Other macromolecular target materials of interest are mucopolysaccharides and polysaccharides derived from or present in microorganisms such as coliform bacteria, salmonellae, shigellae, proteus species, pasteurellae, brucellae, aerobic spore-forming baccilli, anaerobic spore-forming bacilli, mycobacteria, actinomycetes (fungus-like bacteria), spirochetes, mycoplasmas, and the like.

Other target species can include: rickettsia (bacteria-like parasites), chlamydia, fungi, and viruses, including adenoviruses, pox viruses, myxoviruses, reoviruses Types 1-3, hepatitis viruses, and tumor viruses; drugs, metabolites pesticides, pollutants, and the like. Included among them are the alkaloids such as morphine alkaloids (morphine, codeine, heroin, cocaine, benzoyl ecgonine, etc.), ergot alkaloids, steroid alkaloids, and the like. Other drugs of interest include steroids, which include the estrogens and androgens; andrenocortical steroids; bile acids; cardiotonic glycosides; and aglycones, which include digoxin and digoxigenin; the barbiturates, e.g., phenobarbital and secobarbital; aminoalkylbenzenes, which include the amphetamines; cannabinal and tetrahydrocannabinol, vitamins, prostaglandins, antibiotics, nucleosides and nucleotides.

Another group of target compounds includes amino acids and small peptides which include polyiodothyronines, e.g., thyroxine, and triiodothyronine, oxytocin, ACTH, angiotensin, met- and leu-inkephalin, their metabolites and derivatives.

The invention will be further illustrated by the following Examples. These are presented to exemplify methods of practicing this invention and are not to be construed as limiting its scope.

EXAMPLES 1 and 2

Two on-line conductivity cells were constructed by fixing platinum wires through diametrically opposite holes in 50 micron or 75 micron i.d. fused silica capillary tubing (Polymicro Technology, Inc., Phoenix, Ariz. and SGE, Austin, Tex.). These 40 micron i.d. holes were made with a computer-controlled $CO_2$ laser. Under a microscope, two 25 micrometer o.d. Pt wires (California Fine Wire Co., Grover City, Calif.) were placed in the holes exactly opposite to each other in order to minimize the potential difference between these electrodes when a high electrical field strength is applied. The wires were placed so as to give internal surfaces which were continuous. Liquified polyethylene glycol (PEG) (MW 1000, J. T. Baker Chemical Co.) was applied to the area surrounding the electrodes so that they were held temporarily in place. Once the PEG had solidified, it was carefully removed from the outside surface of the capillary. An epoxy (Miller Stephenson 907) was then used to seal permanently the electrodes in the capillary. Wires (#30 wire wrap, Digital Inc.) were soldered to the platinum electrodes and the entire conductivity cell was sealed in a plexiglass jacket. The completed structure of the conductivity cells corresponds to FIGS. 2-4.

The conductivity cells were then used to measure the conductivity of solutions as they were driven through an electrokinetic separation zone as shown in FIG. 5. An AC conductivity meter as shown in FIG. 6 was used. The oscillation frequency was set to 3.5 kHz. A low-pass filter was placed after the circuit to minimize electronic noise. The output of the conductivity meter was amplified (gain: 10 or 20) before being transmitted to a data acquisition board (DT2801, Data Translation, Inc., Marlborough, Mass.) in an IBM XT microcomputer for display.

Samples were introduced either by electromigration for 5 seconds at 5 kV or by gravity flow for 30 seconds with one end of the capillary elevated 10 cm higher than the other. The estimated volume injected was about 10 nL for electromigration and about 5 nL for gravity injection. The capillary was washed with buffer after each run.

Samples containing ions were dissolved in a buffer solution consisting of 20 mM morpholinoethanesulfonic acid (MES) adjusted by histidine to pH 6.1. All chemicals were obtained from Sigma (St. Louis, Mo.) and used without further purification. Serum samples were also tested. These were acquired from the Stanford University Medical Center and diluted, as needed, with buffer solution. The diluted serum samples were deproteinized with a filter membrane (Toya Soda, Japan) in a centrifuge.

RESULTS AND DISCUSSION

Figure 11:
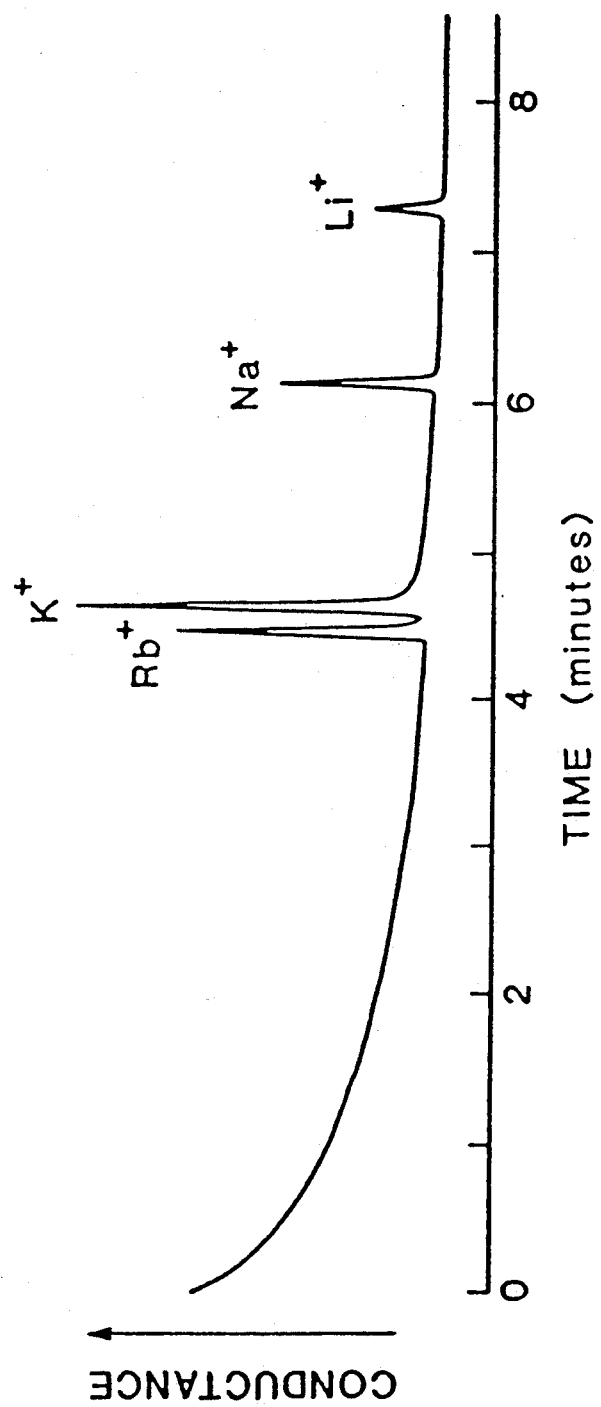
FIGS. 11, 12, 13a and 13b, and 14 are five representative electropherograms showing separations achieved and detected using the present invention.

FIG. 11 depicts the electrophoretic separation and detection of $Rb+$, $K+$, $Na+$, and $Li+$. The concentration of each ion is $2\times10^{-5}M$. The signal-to-noise ratio, at this concentration, is 400. Based on a signal-to-noise ratio of 2, the detection limit is calculated to be about $10^{-7}M$ for $Li+$. The effective detection volume is about 30 pL based on the determination of the cell constant (cross-sectional area of the electrodes divided by the distance between them) made by measuring the conductance of a known solution of KCl and using the literature value of the specific conductance for this solution. This volume estimate assumes that the electrodes are separated by 50 micrometers (the inside diameter of the capillary tube). The value obtained agrees within a factor of 1.5 with the geometrical volume based on the cross-sectional area of the electrodes and the distance between them. This implies that the actual amount detectable is $10^{-18}$ moles, which corresponds to about $10^6$ ions. The retention time of each ion is approximately proportional to the reciprocal of its mobility. All of the peaks shown in FIG. 11 are "positive", i.e., when each of these ions passes the detection electrodes, their conductivities are greater than the background conductivity of the buffer solution and show up as positive deviations above the baseline. Thus, the areas of the peaks represent the mobility differences between the ions in the detection zone and the counter ion (histidine) of the electrolyte. It is also possible to observe "negative" peaks, which are negative deviations from the base line. These occur when a species with less conductivity than the background passes by the sensing electrodes.

Peak areas is linearly related to ion concentration. A correlation-regression analysis was done on 18 concentration levels of $Li+$ extending over 3 orders of magnitude from 0.0025 mM to 2.0 mM. Three consecutive runs were made at each concentration level. The peak areas of $Li+$ were found to be linear over the entire range examined with a correlation coefficient of 0.993. Similar results were obtained for $Na+$.

Figure 12:
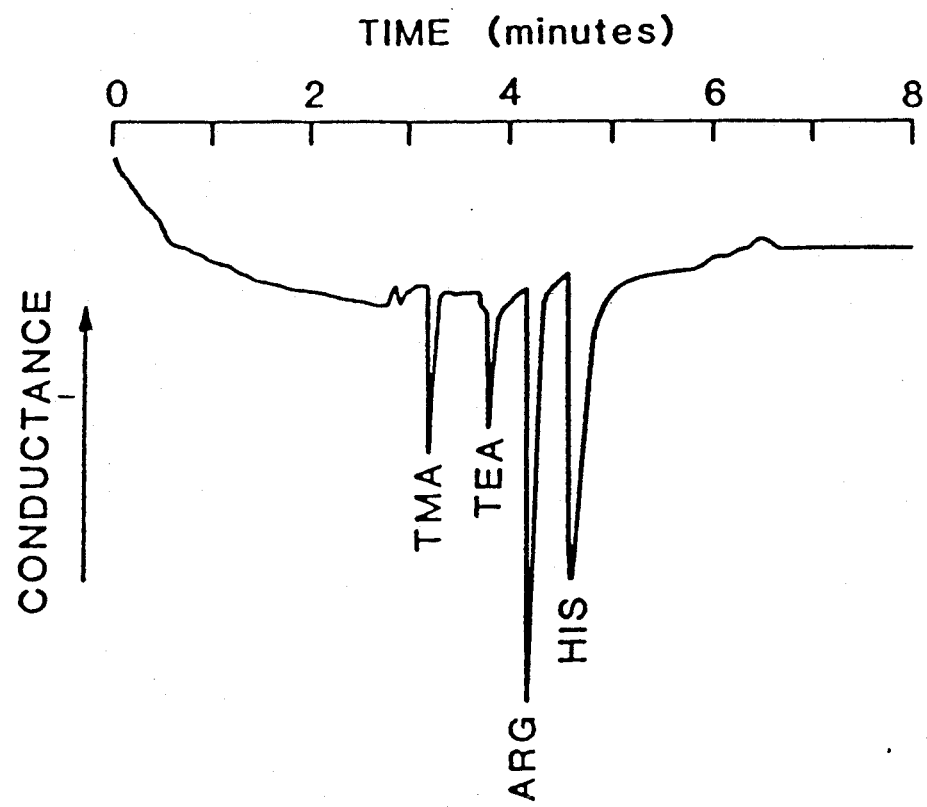

An electropherogram showing the separation of tetramethyl ammonium, triethyl amine, arginine, and histidine is shown in FIG. 12. Since the $K+$, used as the counter ion in the buffer, has a greater mobility than the sample components, the peaks are "negative", i.e., they project below the baseline. This data illustrates that this method can be used to separate some organic cations. By altering buffer conditions, organic anions can also be detected.

Figure 13A:
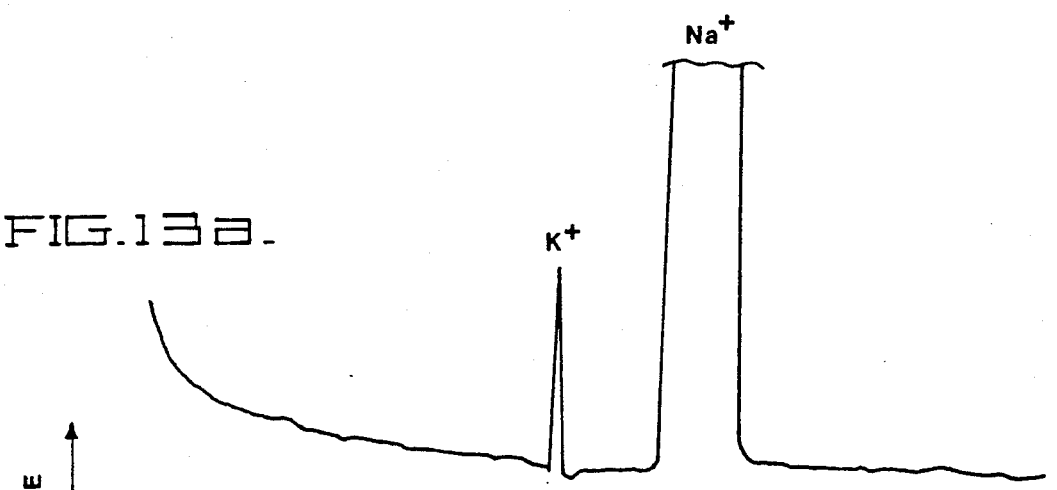
Figure 13B:
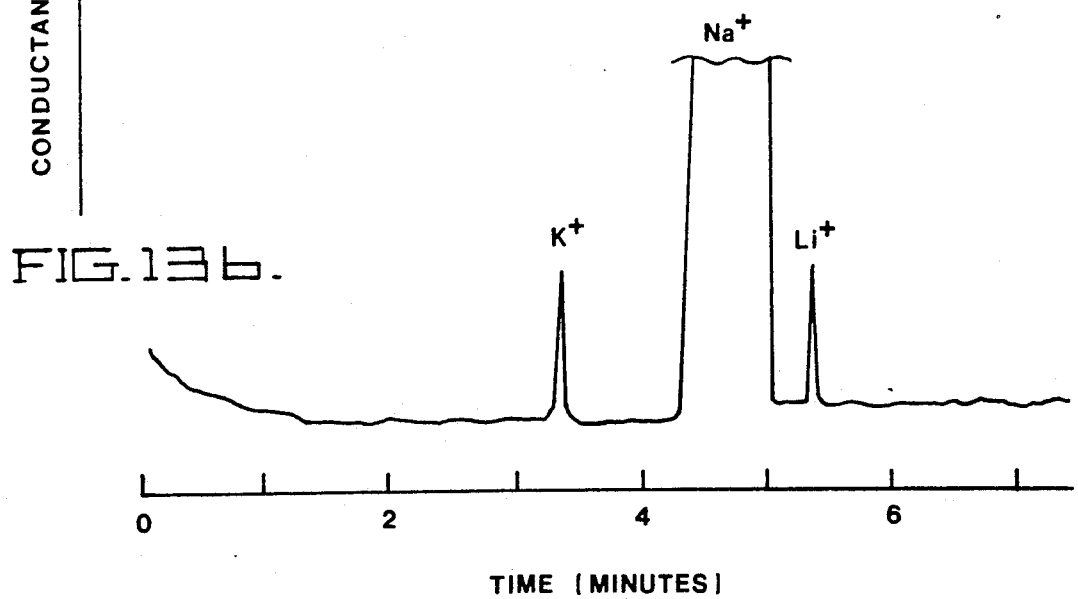

A norman human serum sample was similarly analyzed and the results are shown in FIG. 13a. The first peak is $K+$, the very broad second peak is $Na+$. The peak clipping occurs due to saturation of the electronics because the $Na+$ concentration in serum is so high (about 140 mM). As a result, $Ca^{2+}$ and $Mg^{2+}$, which have mobilities close to that of $Na+$, are obscured by the large Na+ peak. FIG. 13b is an electropherogram of a serum sample from a patient on lithium therapy. It demonstrates that the third (Li+) peak is completely resolved from the Na+ peak. This suggests that this method may be useful in clinically monitoring patients taking lithium therapy.

This new conductivity detector has several advantageous characteristics. It permits control of the deviation of the distance along the capillary between the electrodes to less than 10 micrometers. This means that the potential difference between the two electrodes can be minimized to less than 0.3 V in a 300 V/cm electric field. This feature eliminates almost completely any electrochemical reactions occurring at the electrodes. Another advantage of this structural form is that excellent resolution is made possible by the very small cross-sectional area of the electrodes. There is essentially no dead volume in the detector and the detection volume is very tiny. This system can be used not only for the detection of charged particles, but can also detect any neutral substances that can be separated electrophoretically. Since the conductivity change is an electrical signal, it is easily coupled to a data acquisition system. The apparatus is economical in terms of both cost and energy. The cost for all of the materials necessary for the construction of the conductivity cell and its associated circuitry is very modest, and the power required is only a few watts which could be furnished by a battery system. Hence, the entire system is readily made portable. Indeed, its small size suggests that it can be readily adapted to in vivo sampling. The sensitivity of this detector is quite remarkable for a non-optical system.

EXAMPLE 3

A capillary zone electrophoretic separation run was carried out using the detector of FIGS. 7 and 8 having a single electrode within the capillary tube and the other electrode outside the capillary tube. A 75 micron i.d., 73.5 cm long fused silica capillary was used. The on-column electrode was about 150 microns from the out end of the capillary. The sample included the amino acid, arginine at a concentration of $5 \times 10^{-4}$ M in 10 mM HEPES (N-2-hydroxyethylpiperazine-N'-2-ethanesulfonic acid) buffer, pH 7.5. Electrokinetic injection was used to introduce the sample into the capillary tube. Injection was made at 5 kV for 5 seconds. The separation run was made using 24 kV and 3 microamps.

Figure 14:
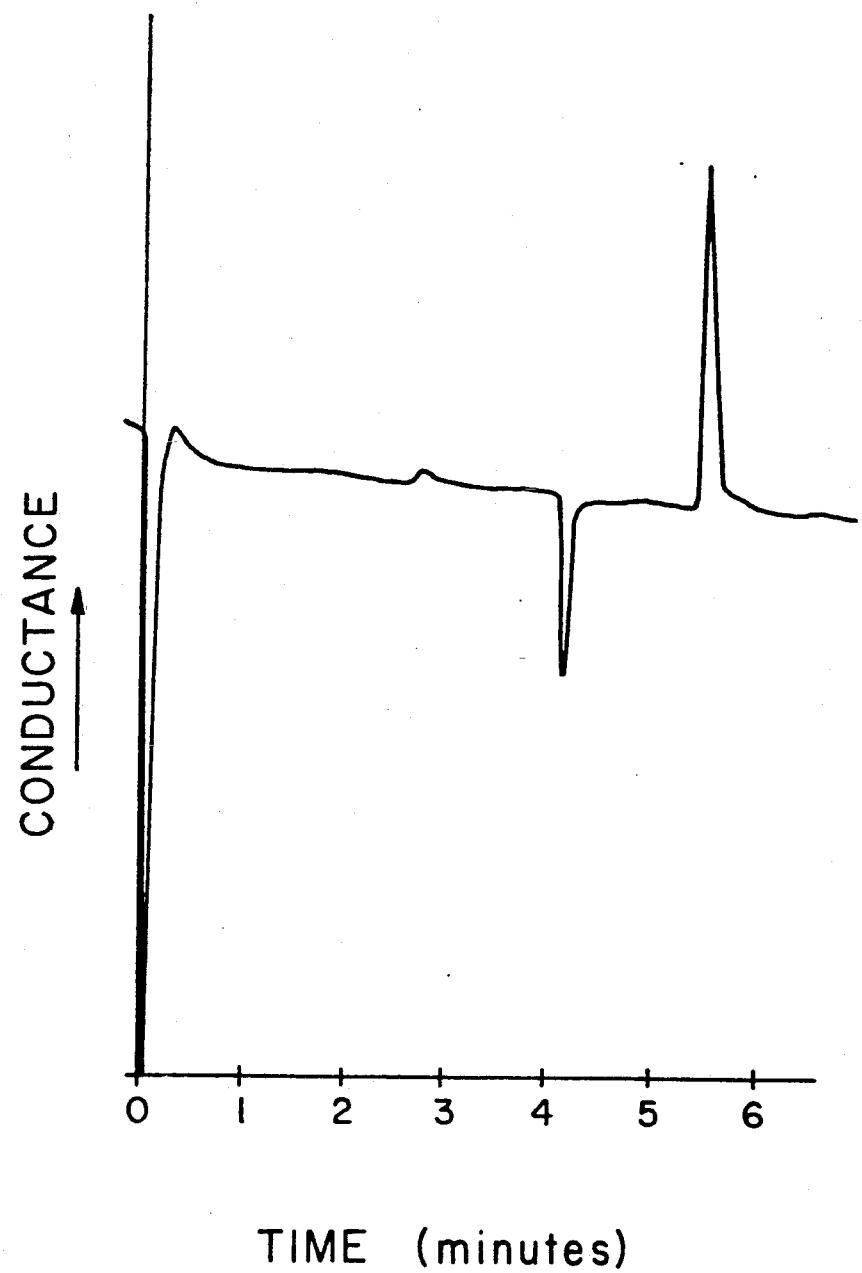

The results of this experiment are shown in FIG. 14, a recorder chart curve showing the conductivity changes detected by the detector of the invention. The sample was injected at about time=0. The negative peak at time=4.2 minutes is the neutral origin while the positive peak at 5.5 minutes is chloride ion.

We claim as our invention:

1. An electrokinetic separation zone comprising a generally cylindrical tubular electrokinetic separation microcolumn having a wall defining an about 25 to about 200 micron diameter microcolumn channel and one or more on-column conductivity electrodes that pass through the microcolumn wall wherein each electrode has a tip that is substantially flush with said wall or that terminates in said microcolumn channel, with each electrode presenting a non-increasing cross-sectional area to the microcolumn channel through the column and wherein the on-column electrodes are located within 500 microns of the exit end of the column.

2. The electrokinetic separation zone as defined in claim 1 wherein the microcolumn is made from inorganic materials selected from the group consisting of quartz, glass, and fused silica.

3. The electrokinetic separation zone as defined in claim 2 wherein the microcolumn channel defines a fluid flow zone.

4. The electrokinetic separation zone as defined in claim 2 wherein each electrode tip has a diameter equal to from about 0.01 to about 0.75 times the diameter of the microcolumn channel.

5. The electrokinetic separation zone as defined in claim 1 having a pair of on-column electrodes wherein the pair of electrodes comprises a first electrode having a first tip and a second electrode having a second tip wherein the first electrode tip is located directly across from the second electrode tip, and wherein each electrode tip is in electrical communication with the contents of the column.

6. An electrokinetic separation zone comprising a generally cylindrical tubular electrokinetic separation microcolumn having a wall defining an about 25 to about 200 micron diameter microcolumn channel and one on-column conductivity electrode that passes through the microcolumn wall and that has a tip that is substantially flush with said wall or that terminates in said microcolumn channel, with said electrode presenting a non-increasing cross-sectional area to the microcolumn channel through the column, wherein the on-column electrode is located within 500 microns of the exit end of the column.

7. The electrokinetic separation zone as defined in claim 6 wherein the microcolumn is made from inorganic materials selected from the group consisting of quartz, glass, and fused silica.

8. The electrokinetic separation zone as defined in claim 7 wherein the microcolumn channel defines a fluid flow zone.

9. The electrokinetic separation zone as defined in claim 7 wherein the electrode tip has a diameter equal to from about 0.01 to about 0.75 times the diameter of the microcolumn channel.

10. An electrokinetic separation zone including conductivity detector means for detecting the passage of species through said zone comprising a cylindrical column having an inner wall defining a narrow bore with an internal diameter of less than 500 microns said column being open on each end and capable of passing liquid therethrough and one or more on-column electrodes each having a contact surface in electrical communication with the contents of the column and each of said electrodes having a diameter equal to from about 0.01 to about 0.75 times the largest internal diameter of the column, wherein each of said electrodes has a tip that is substantially flush with said inner wall or that terminates in said narrow bore, and wherein the column is made of inorganic materials.

11. The electrokinetic separation zone as defined in claim 10 wherein the microcolumn is made from inorganic materials selected from the group consisting of quartz, glass, and fused silica.

12. The electrokinetic separation zone of claim 11 having a single on-column electrode, located within 500 microns of the exit end of the column.

13. The electrokinetic separation zone of claim 10 having at least one pair of on-column electrodes wherein each said pair of electrodes has a first electrode having a first tip and a second electrode having a second tip wherein the first electrode tip is located directly across from the second electrode tip, and wherein each electrode tip is in electrical communication with the contents of the column.

14. A method for manufacturing an on-column conductivity detector for electrokinetic separation comprising the steps of:
 a. forming one or more access holes through a cylindrical tubular microcolumn;
 b. inserting an electrode into each of the holes formed; and
 c. permanently sealing the electrodes to the microcolumn.

15. A method for manufacturing the detector as defined in claim 14 wherein the step of forming the access holes comprises laser drilling, ion beam drilling, electroerosion, or chemical etching.

16. A method for manufacturing an on-column conductivity detector for electrokinetic separation comprising the steps of:
 a. forming one or more access holes through a vitreous cylindrical tubular microcolumn with a laser drill;
 b. inserting an electrode into each of the holes formed; and
 c. permanently sealing the electrodes to the microcolumn.

17. A method for manufacturing an on-column conductivity detector for electrokinetic separation comprising the steps of:
 a. forming one or more access holes through a cylindrical tubular microcolumn wherein the inner diameter of the microcolumn is less than about 500 microns, preferably less than 200 microns, and more preferably from about 25 to 80 microns;
 b. inserting an electrode into each of the holes formed wherein the electrodes have a diameter equal to from about 0.01 to about 0.75, and especially from about 0.01 to about 0.60 times the inner diameter of the microcolumn, and wherein the access holes are formed to a size from about 5 to about 25 microns in diameter larger than the diameter of the electrode being inserted therein; and
 c. permanently sealing the electrodes to the microcolumn.

18. A method for manufacturing an on-column conductivity detector for electrokinetic separation comprising the steps of:
 a. forming one or more access holes through a vitreous cylindrical tubular microcolumn with a laser drill wherein the inner diameter of the microcolumn is less than about 500 microns, preferably less than 200 microns, and more preferably from about 25 to 80 microns;
 b. inserting an electrode into each of the holes formed wherein the electrodes have a diameter equal to from about 0.01 to about 0.75, and especially from about 0.01 to about 0.60 times the inner diameter of the microcolumn, and wherein the access holes are formed to a size from about 5 to about 25 microns in diameter larger than the diameter of the electrode being inserted therein; and
 c. permanently sealing the electrodes to the microcolumn.

* * * * *